United States Patent [19]

Yamashita et al.

[11] Patent Number: 5,663,397
[45] Date of Patent: Sep. 2, 1997

[54] CYCLIC SILYL ENOL ETHERS AND METHOD OF PREPARING THE SAME

[75] Inventors: Hiroshi Yamashita; Masato Tanaka, both of Tsukuba, Japan

[73] Assignee: Director-General of Agency of Industrial Science and Technology, Tokyo, Japan

[21] Appl. No.: 713,759

[22] Filed: Sep. 13, 1996

[30] Foreign Application Priority Data

Sep. 14, 1995 [JP] Japan .................................. 7-236329
Mar. 8, 1996 [JP] Japan .................................. 8-51125

[51] Int. Cl.$^6$ .................................. C07F 7/08; C07F 7/18
[52] U.S. Cl. .................................. 556/464; 549/4; 549/214; 549/215
[58] Field of Search .................................. 556/464, 4, 214, 556/215

[56] References Cited

U.S. PATENT DOCUMENTS

| | | | |
|---|---|---|---|
| 3,337,598 | 8/1967 | Sterling et al. | 556/464 |
| 4,528,389 | 7/1985 | Farnham | 556/464 X |
| 5,124,468 | 6/1992 | Krafft et al. | 556/464 X |
| 5,191,102 | 3/1993 | Oyama | 556/464 |

*Primary Examiner*—Paul F. Shaver
*Attorney, Agent, or Firm*—Birch, Stewart, Kolasch & Birch, LLP

[57] ABSTRACT

There is disclosed a method of preparing cyclic silyl enol ethers (1-oxa-2-sila-5-cyclohexenes), comprising reacting a silacyclobutane with an acid halide in the presence of a palladium catalyst and an organic base. There is also disclosed novel cyclic silyl enol ethers obtained by the above method. The above cyclic silyl enol ethers belong to a new class of silyl enol ethers which are useful in the production of medicines and agricultural chemicals, and they can be used as intermediates of fine chemicals or as various reagents for fine synthesis.

17 Claims, No Drawings

CYCLIC SILYL ENOL ETHERS AND METHOD OF PREPARING THE SAME

FIELD OF THE INVENTION

The present invention relates to a novel method of preparing cyclic silyl enol ethers by the reaction of silacyclobutanes with acid halides, and to novel silicon compounds obtained thereby.

The cyclic silyl enol ethers provided by the present invention belong to a new class of silyl enol ethers which are useful in the production of medicines (pharmaceuticals) and agricultural chemicals, and they can be used as intermediates of fine chemicals or as various reagents for fine synthesis. (For example, they can be used by converting them to compounds having an end hydroxyl group through an elimination step of the $>Si(R^1)(R^2)$ group. Also see "Silicon Reagents for Organic Synthesis," by W. P. Weber, Springer-Verlag (1983), Sections 12 to 15.)

BACKGROUND OF THE INVENTION

The cyclic silyl enol ethers according to the present invention are novel compounds, and therefore no examples are known for the production thereof.

SUMMARY OF THE INVENTION

An object of the present invention is to provide a novel method of effectively preparing cyclic silyl enol ethers.

Another object of the present invention is to provide novel silicon compounds produced by the above method.

Other and further objects, features, and advantages of the invention will appear more fully from the following description.

DETAILED DESCRIPTION OF THE INVENTION

The present inventors, having studied intensively to attain the above objects, have found a novel fact that silacyclobutanes react readily with readily available acid halides, in the presence of a palladium catalyst and an organic base, to give cyclic silyl enol ethers in high yields, together with the salt of the organic base and hydrogen halide. The present invention has been made based on the above finding.

That is, the present invention provides:

(1) A method of preparing cyclic silyl enol ethers represented by the following formula (IV):

Formula (IV)

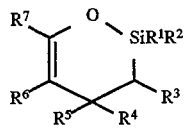

wherein $R^1$ and $R^2$, which are the same or different, each represent a monovalent group selected from an alkyl group, an aryl group, and an aralkyl group; $R^3$, $R^4$, $R^5$, and $R^6$, which are the same or different, each represent a monovalent group selected from a hydrogen atom, an alkyl group, and an aryl group; and $R^7$ represents an aryl group, an alkenyl group, an alkyl group, or a monovalent heterocyclic group, or by the following formula (V-a) or (V-b):

Formula (V-a), (V-b)

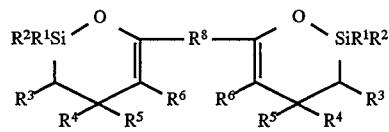

or

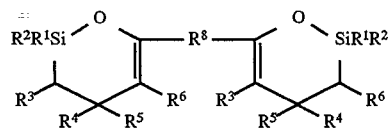

wherein $R^1$, $R^2$, $R^3$, $R^4$, $R^5$, and $R^6$ are as defined above, and $R^8$ represents an arylene group, an alkenylene group, an alkylene group, or a divalent heterocyclic group, comprising reacting a silacyclobutane represented by the following formula (I):

Formula (I)

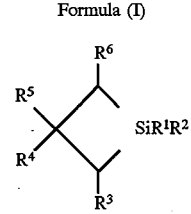

wherein $R^1$, $R^2$, $R^3$, $R^4$, $R^5$, and $R^6$ have the same meanings as defined above in formula (IV), (V-a), or (V-b), with an acid halide represented by the following formula (II):

Formula (II)

wherein $R^7$ has the same meaning as defined above in formula (IV), and X represents a halogen atom, or by the following formula (III):

Formula (III)

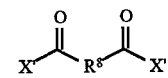

wherein $R^8$ has the same meaning as defined above in formula (V-a) or (V-b), and X' represents a halogen atom, in the presence of a palladium catalyst and an organic base.

(2) A cyclic silyl enol ether represented by the following formula (VI):

Formula (VI)

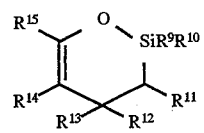

wherein $R^9$ and $R^{10}$, which are the same or different, each represent a monovalent group selected from an alkyl group, an aryl group, and an aralkyl group; $R^{11}$, $R^{12}$, $R^{13}$, and $R^{14}$, which are the same or different, each represent a monovalent group selected from a hydrogen atom, an alkyl group, and an aryl group; and $R^{15}$ represents an aryl group, an alkenyl group, an alkyl group, or a monovalent heterocyclic group, or by the following formula (VII-a) or (VII-b):

Formula (VII-a), (VII-b)

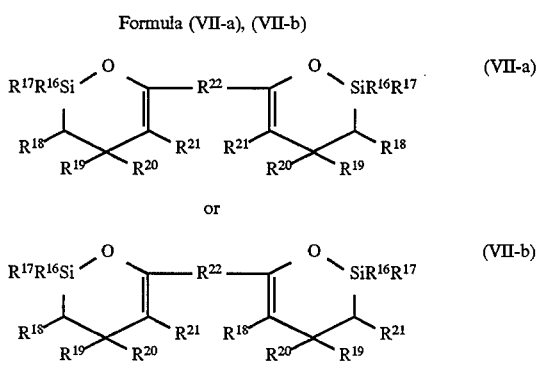

wherein $R^{16}$ and $R^{17}$, which are the same or different, each represent a monovalent group selected from an alkyl group, an aryl group, and an aralkyl group; $R^{18}$, $R^{19}$, $R^{20}$, and $R^{21}$, which are the same or different, each represent a monovalent group selected from a hydrogen atom, an alkyl group, and an aryl group; and $R^{22}$ represents an arylene group.

PREFERRED EMBODIMENT OF THE INVENTION

According to the present invention, there are provided a method of preparing cyclic silyl enol ethers represented by the above formula (IV), (V-a), or (V-b), comprising reacting a silacyclobutane represented by the above formula (I) with an acid halide represented by the above formula (II) or (III), in the presence of a palladium catalyst and an organic base; and the present invention provides novel silicon compounds obtained thereby.

In formula (I), the substituents $R^1$ and $R^2$ on the silicon each represent an alkyl group, an aryl group, or an aralkyl group; and more particularly they represent an alkyl group having preferably 1 to 20 carbon atoms, and more preferably 1 to 8 carbon atoms, an aryl group having preferably 6 to 20 carbon atoms, and more preferably 6 to 10 carbon atoms, or an aralkyl group having preferably 7 to 20, and more preferably 7 to 10 carbon atoms. Specific examples of them are a methyl group, an ethyl group, an isopropyl group, a pentyl group, an octyl group, a phenyl group, a naphthyl group, a benzyl group, and a phenethyl group. $R^3$, $R^4$, $R^5$, and $R^6$ each represent a hydrogen atom, an alkyl group, or an aryl group; and more particularly they represent a hydrogen atom, an alkyl group having preferably 1 to 10 carbon atoms, and more preferably 1 to 4 carbon atoms, or an aryl group having preferably 6 to 20 carbon atoms, and more preferably 6 to 10 carbon atoms; and besides a hydrogen atom, as examples, a methyl group, a butyl group, a phenyl group, and a naphthyl group can be mentioned. Therefore, examples of the silacyclobutane represented by formula (I) having these substituents and the like include 1,1-dimethyl-1-silacyclobutane, 1,1-diethyl-1-silacyclobutane, 1-methyl-1-isopropyl-1-silacyclobutane, 1,1-dipentyl-1-silacyclobutane, 1-methyl-1-phenyl-1-silacyclobutane, 1,1-diphenyl-1-silacyclobutane, 1-methyl-1-naphthyl-1-silacyclobutane, 1,1-dibenzyl-1-silacyclobutane, 1-methyl-1-phenethyl-1-silacyclobutane, 1,1,2-trimethyl-1-silacyclobutane, 1,1,2,4-tetramethyl-1-silacyclobutane, 1,1,3,3-tetramethyl-1-silacyclobutane, 1,1-dimethyl-3-phenyl-1-silacyclobutane, and 3-methyl-1,1-diphenyl-1-silacyclobutane.

$R^7$ in formula (II) represents an aryl group, an alkenyl group, an alkyl group, or a monovalent heterocyclic group; and more particularly it represents an aryl group having preferably 6 to 20 carbon atoms, and more preferably 6 to 10 carbon atoms, an alkenyl group having preferably 2 to 20 carbon atoms, and more preferably 2 to 12 carbon atoms, an alkyl group having preferably 1 to 20 carbon atoms, and more preferably 1 to 12 carbon atoms; or it represents a preferably 3-membered to 10-membered, more preferably a 5-membered to 8-membered, monovalent heterocyclic group having at least one heteroatom selected from oxygen atom, nitrogen atom, sulfur atom, selenium atom, silicon atom, boron atom, and the like. Examples thereof include a phenyl group, a naphthyl group, a vinyl group, a styryl group, a decenyl group, a 2-phenylethyl group, an isopropyl group, a hexyl group, a cyclohexyl group, a tert-butyl group, a furyl group, and a thienyl group, part of the hydrogen atoms of which may be replaced by a substituent(s), such as an alkyl group, an alkoxy group, an aryl group, and a halogen atom. Examples of X are a chlorine atom, a bromine atom, and an iodine atom. As the acid halide represented by formula (II) having, for example, these substituents, can be mentioned benzoyl chloride, benzoyl bromide, benzoyl iodide, toluoyl chloride, fluorobenzenecarbonyl chloride, methoxybenzenecarbonyl chloride, naphthoyl chloride, acryloyl chloride, cinnamoyl chloride, 10-undecenoyl chloride, hydrocinnamoyl chloride, isopropionyl chloride, heptanoyl chloride, cyclohexanecarbonyl chloride, furoyl chloride, and thenoyl chloride.

$R^8$ in formula (III) represents an arylene group, an alkenylene group, an alkylene group, or a divalent heterocyclic group; and more particularly it represents an arylene group having preferably 6 to 20 carbon atoms, and more preferably 6 to 10 carbon atoms, an alkenylene group having preferably 2 to 20 carbon atoms, and more preferably 2 to 10 carbon atoms, an alkylene group having preferably 1 to 20 carbon atoms, and more preferably 1 to 8 carbon atoms; or it represents a preferably 3-membered to 10-membered, and more preferably a 5-membered to 8-membered, divalent heterocyclic group having at least one heteroatom selected from oxygen atom, nitrogen atom, sulfur atom, selenium atom, silicon atom, boron atom, and the like. Examples thereof include a phenylene group, a naphthylene group, a vinylene group, a propenylene group, a methylmethylene group, a 1,2-dimethylethylene group, a 1,3-diethyltrimethylene group, a furylene group, and a thienylene group. Examples of X' include those of X. Therefore, examples of the acid halide represented by formula (III) are terephthaloyl dichloride, naphthalenedicarbonyl dichloride, and isophthaloyl dibromide.

In the method of preparing cyclic silyl enol ethers of the present invention, the molar ratio of the silacyclobutane to the acid halide to be reacted can be optionally chosen, and taking the yield from the acid halide into account, desirably the molar ratio of the silacyclobutane to the haloformyl group in the acid halide is 1 or more, and generally it is from 1 to 2.

Further, as the palladium catalyst to be used, various palladium catalysts, including those which are conventional, such as palladium complexes, palladium metal salts, palladium metal, or supported palladium metal, can be used. Specific examples thereof include dichloro(1,5-cyclooctadiene)palladium, bis(dibenzylideneacetone) palladium, tris(dibenzylideneacetone)dipalladium, dichlorobis(benzonitrile)palladium, dibromobis(benzonitrile)palladium, dichlorobis(acetonitrile)palladium, di-μ-chlorobis(π-allyl)dipalladium, dichlorobis(pyridine)palladium, dichlorobis(triphenylphosphine)palladium, diiodobis(dimethylphenylphosphine)palladium, dichlorobis(triethylphosphine)palladium, dichlorobis(trimethylphosphine)palladium, dichlorobis (trimethylphosphite)palladium, dibromo(triisopropylphosphite)palladium, dichlorobis(triphenylphosphite)palladium, dichlorobis(dimethoxyethylphosphine)palladium, dichloro[1,4-bis(diphenylphosphino)butane]palladium, tetrakis(triphenylphosphine)palladium, palladium acetate, palladium chloride, palladium iodide, and palladium supported on active carbon. Two or more of these palladium catalysts can be used in combination with each other. Further, these palladium catalysts can be used with a ligand component that is contained in the above mentioned metal compounds.

The molar ratio of the palladium catalyst to the silacyclobutane or the acid halide can be chosen optionally, and the ratio is generally in the range of from 0.0001 to 0.5.

On the other hand, as the organic base to be used in the present invention, generally amines can be used. Examples thereof include triethylamine, tributylamine, diisopropylethylamine, isopropyldiethylamine, dicyclohexylmethylamine, dicyclohexylethylamine, N-methylpyrrolidine, and 1,8-diazabicyclo-[5,4,0]undec-7-ene (DBU). Taking the yield of the cyclic silyl enol ethers that will be obtained into account, the molar ratio of the base to the haloformyl group in the acid halide is preferably 1 or more, and generally it is from 1 to 10.

The reaction of the present invention is carried out at a reaction temperature of −20° C. or higher, preferably 0° to 200° C. The method of the present invention can be carried out with or without a solvent. If any solvent is used, various organic solvents, such as hydrocarbon solvents, for example, benzene, toluene, xylene, hexane, and decalin, and ether solvents, for example, dibutyl ether, except those that will react with the silacyclobutane and/or the acid halide that are raw materials, can be used.

The separation and purification of the intended product from the reaction mixture can be readily attained by a means that is generally used in organic chemistry, such as distillation, chromatography, and recrystallization.

On the other hand, the novel silicon compounds provided by the present invention are cyclic silyl enol ethers represented by formula (VI), (VII-a), or (VII-b). The substituents $R^9$, $R^{10}$, $R^{16}$, and $R^{17}$ on the silicon in formula (VI), (VII-a), and (VII-b) have the same meanings as those of the substituents $R^1$ and $R^2$ in formula (I), and examples thereof are a methyl group, an ethyl group, an isopropyl group, a pentyl group, an octyl group, a phenyl group, a naphthyl group, a benzyl group, and a phenethyl group. $R^{11}$, $R^{12}$, $R^{13}$, $R^{14}$, $R^{18}$, $R^{19}$, $R^{20}$, and $R^{21}$ have the same meanings as those of the substituents $R^3$, $R^4$, $R^5$, and $R^6$ in formula (I), and examples thereof are a hydrogen atom, a methyl group, and a phenyl group.

On the other hand, $R^{15}$ in formula (VI) has the same meaning as that of $R^7$ in formula (II), and examples thereof are a phenyl group, a tolyl group, an anisyl group, a fluorophenyl group, a naphthyl group, a vinyl group, a styryl group, a decenyl group, a 2-phenylethyl group, an isopropyl group, a hexyl group, a cyclohexyl group, a tert-butyl group, a furyl group, and a thienyl group. Therefore, specific examples of the cyclic silyl enol ethers represented by formula (VI) having those substituents and the like are 2,2-dimethyl-6-phenyl-1-oxa- 2-sila-5-cyclohexene, 2,2-dimethyl-6-tolyl-1-oxa-2-sila-5-cyclohexene, 2,2-dimethyl-6-anisyl-1-oxa-2-sila-5-cyclohexene, 2,2-dimethyl-6-fluorophenyl-1-oxa-2-sila-5-cyclohexene, 2,2-dimethyl-6-naphthyl-1-oxa-2-sila-5-cyclohexene, 2,2-dimethyl-6-cyclohexyl-1-oxa-2-sila-5-cyclohexene, 2,2-dimethyl-6-furyl-1-oxa-2-sila-5-cyclohexene, 2,2-dimethyl-6-thienyl-1-oxa-2-sila-5-cyclohexene, 2-methyl-2,6-diphenyl-1-oxa-2-sila-5-cyclohexene, 2,2-diphenyl-6-tolyl-1-oxa-2-sila-5-cyclohexene, 2,2-dimethyl-6-styryl-1-oxa-2-sila-5-cyclohexene, 2,2,6-triphenyl-1-oxa-2-sila-5-cyclohexene, 2,2-dimethyl-6-hexyl-1-oxa-2-sila-5-cyclohexene, 2,2-dimethyl-6-(2-phenylethyl)-1-oxa-2-sila-5-cyclohexene, and 2,2-dimethyl-6-(9-decenyl)-1-oxa-2-sila-5-cyclohexene.

$R^{22}$ in formulae (VII-a) and (VII-b) represents an arylene group, and examples thereof are a phenylene group and a naphthylene group. Therefore, specific examples of the cyclic silyl enol ethers represented by formula (VII-a) or (VII-b) having these substituents or the like are bis(2,2-dimethyl-1-oxa-2-sila-5-cyclohexen-6-yl)-p- or -m-phenylene, and bis(2,2-dimethyl-1-oxa-2-sila-5-cyclohexen-6-yl)-1,4- or 1,5-naphthylene.

According to the method of the present invention, various cyclic silyl enol ethers that are highly valuable in organic synthesis can be produced efficiently without environmental or operation problems (i.e. the reaction conditions are mild, reagents which are harmful are not employed, and no hazardable by-products are produced) from silacyclobutanes and readily available acid halides, and their separation and purification are easy. Also by the present invention, novel cyclic silyl enol ethers are provided. Therefore, the present invention is industrially very significant.

EXAMPLE

Now, the present invention will be described in more detail with reference to examples, but the present invention is not limited to these examples.

Example 1

A mixture of 2.0 mmol of 1,1-dimethyl-1-silacyclobutane, 2.0 mmol of benzoyl chloride, 4.0 mmol of triethylamine, 0.08 mmol of dichlorobis(benzonitrile)palladium, and 2 ml of toluene was stirred in a Schlenk tube under nitrogen at 80° C. for 4 hours. By measuring the reaction solution by NMR, it was estimated that 2,2-dimethyl-6-phenyl-1-oxa-2-sila-5-cyclohexene was produced in a yield of 92%. The reaction mixture was concentrated under reduced pressure, and the product was extracted with ~10 ml of hexane. The hexane extract was concentrated under reduced pressure, followed by distillation using a Kügelrohr, thereby obtaining 1.6 mmol (an isolated yield of 80%) of the above intended product.

This compound is a novel compound that has not yet appeared in the literature, and the values of the physical properties and the spectral data thereof are as follows:

Boiling point: 122°–130° C./5 mmHg (Kügelrohr). $^1$H-NMR ($C_6D_6$, TMS): δ 0.15 (s, 6H, Si($CH_3$)$_2$), 0.63 (t, J=7.1 Hz, 2H, SiCH$_2$), 2.27 (td, J=7.1, 4.9 Hz, 2H, SiCCH$_2$), 5.39 (t, J=4.9 Hz, 1H, CH=), 7.07–7.80 (m, 5H, $C_6H_5$). $^{13}$C-NMR ($C_6D_6$, TMS): δ −1.1 (SiCH$_3$), 9.5 (SiCH$_2$), 19.7 (SiCC), 101.7 (CH=), 124.9 (o-C), 127.7 (p-C), 128.3 (m-C), 138.5 (ipso-C), 150.9 (O—C=). $^{29}$Si-NMR ($C_6D_6$, TMS): δ 18.2. IR (liquid film): 1636 (C=C), 1235 (SiMe), 1089 (SiO) cm$^{-1}$. MS (EI, 70 eV): m/z 204 (100, M$^+$), 203 (93), 189 (71), 130 (72), 129 (55), 115 (29), 87 (30), 77 (24), 75 (52), 61 (22), 59 (25), 45 (28), 43 (25). Elementary analysis for $C_{12}H_{16}OSi$ Found: C, 70.19%; H, 7.90% Calculated: C, 70.53%; H, 7.89%

Example 2

The reaction and analysis of Example 1 were repeated, except that, instead of dichlorobis(benzonitrile)palladium, dichlorobis(triphenylphosphine)palladium was used as a catalyst. From the result of the NMR analysis, it was estimated that 2,2-dimethyl-6-phenyl-1-oxa-2-sila-5-cyclohexene was produced in a yield of 78%.

Examples 3 to 8

Example 1 was repeated, except that different acid halides were used. The results are shown in Table 1.

2,2-dimethyl-6-(p-anisyl)-1-oxa-2-sila-5-cyclohexene (product of Example 4)

Boiling point: 130°–137° C./7 mmHg (Kügelrohr). $^1$H-NMR ($C_6D_6$, TMS): δ 0.17 (s, 6H, Si($CH_3$)$_2$), 0.66 (t, J=7.1 Hz, 2H, Si$CH_2$), 2.31 (td, J=7.1, 4.9 Hz, 2H, SiC$CH_2$), 3.32 (s, 3H, O$CH_3$), 5.31 (t, J=4.9 Hz, 1H, CH=), 6.75–6.83 and 7.61–7.70 (m respectively, 2H respectively, $C_6H_4$). $^{13}$C-NMR ($C_6D_6$, TMS): δ −1.0 (Si$CH_3$), 9.6 (Si$CH_2$), 19.7 (SiC$\underline{C}$), 54.7 (O$CH_3$), 99.9 (CH=), 113.7 and 126.2

TABLE 1

| Example[1] | Acid halide | Product | Yield[2] (%) |
|---|---|---|---|
| Example 3 | CH$_3$—⟨C$_6$H$_4$⟩—COCl | CH$_3$—⟨C$_6$H$_4$⟩—CH=CH—CH$_2$—CH$_2$—Si(CH$_3$)$_2$—O (cyclic) | 93 (80) |
| Example 4 | CH$_3$O—⟨C$_6$H$_4$⟩—COCl | CH$_3$O—⟨C$_6$H$_4$⟩—CH=CH—CH$_2$—CH$_2$—Si(CH$_3$)$_2$—O (cyclic) | 99 |
| Example 5 | F—⟨C$_6$H$_4$⟩—COCl | F—⟨C$_6$H$_4$⟩—CH=CH—CH$_2$—CH$_2$—Si(CH$_3$)$_2$—O (cyclic) | 98 |
| Example 6 | furyl—COCl | furyl—CH=CH—CH$_2$—CH$_2$—Si(CH$_3$)$_2$—O (cyclic) | 86 |
| Example 7 | Ph—CH=CH—COCl | Ph—CH=CH—CH=CH—CH$_2$—CH$_2$—Si(CH$_3$)$_2$—O (cyclic) | 97 |
| Example 8 | cyclohexyl—COCl | cyclohexyl—CH=CH—CH$_2$—CH$_2$—Si(CH$_3$)$_2$—O (cyclic) | 94 (79) |

[1] Reaction conditions: 2.0 mmol of 1,1-dimethyl-1-silacyclobutane, 2.0 mmol of an acid halide, 4.0 mmol of triethylamine, 0.08 mmol of dichlorobis(benzonitrile)-palladium, and 2 ml of toluene, at 80° C. for 4 hours.
[2] Yield of the reaction product measured by NMR. In the parentheses, the isolated yields are shown.

The compounds obtained in Examples 3 to 8 shown in Table 1 are novel compounds that have not yet appeared in literature, and the values of the physical properties and the spectral data thereof are as follows:

2,2-dimethyl-6-(p-tolyl)-1-oxa-2-sila-5-cyclohexene (product of Example 3)

Boiling point: 130°–137° C./5 mmHg (Kügelrohr). $^1$H-NMR ($C_6D_6$, TMS): δ 0.16 (s, 6H, Si($CH_3$)$_2$), 0.64 (t, J=7.1 Hz, 2H, Si$CH_2$), 2.12 (s, 3H, $CCH_3$), 2.29 (td, J=7.1, 4.9 Hz, 2H, SiC$CH_2$), 5.40 (J=4.9 Hz, 1H, CH=), 7.01–7.72 (m, 4H, $C_6H_4$). $^{13}$C-NMR ($C_6D_6$, TMS): δ −1.0 (Si$CH_3$), 9.6 (Si$CH_2$), 19.7 (Si$\underline{C}$$\underline{C}$), 21.1 ($CCH_3$), 100.8 (CH=), 124.9 and 129.0 (tertiary C of benzene ring), 135.8 and 137.1 (quaternary C of benzene ring), 151.1 (O—C=). $^{29}$Si-NMR ($C_6D_6$, TMS): δ 18.0 IR (liquid film): 1686 (C=C), 1255 (SiMe), 1087 (SiO) cm$^{-1}$. MS (EI, 70 eV): m/z 218 (50, M$^+$), 217 (29), 203 (100), 129 (31), 75 (20). Elementary analysis for $C_{13}H_{18}OSi$ Found: C, 71.51%; H, 8.36% Calculated: C, 71.50%; H, 8.31%

(tertiary C of benzene ring), 131.2 (quaternary C of benzene ring), 150.8 (O—C=), 159.8 (quaternary C of benzene ring). $^{29}$Si-NMR ($C_6D_6$, TMS): δ 18.0 IR (liquid film): 1680 (C=C), 1259 (SiMe), 1055 (SiO) cm$^{-1}$. MS (EI, 70 eV): m/z 234 (100, M$^+$), 233 (83), 219 (66), 203 (34), 160 (24), 159 (32), 102 (28), 75 (27). Elementary analysis for $C_{13}H_{18}O_2Si$ Found: C, 66.56%; H, 7.82% Calculated: C, 66.62%; H, 7.74%

2,2-dimethyl-6-(p-fluorophenyl)-1-oxa-2-sila-5-cyclohexene (product of Example 5)

Boiling point: 99°–107° C./7 mmHg (Kügelrohr). $^1$H-NMR ($C_6D_6$, TMS): δ 0.13 (s, 6H, Si($CH_3$)$_2$), 0.61 (t, J=7.1 Hz, 2H, Si$CH_2$), 2.24 (td, J=7.1, 4.9 Hz, 2H, SiC$CH_2$), 5.19 (t, J=4.9 Hz, 1H, CH=), 6.77–6.88 and 7.40–7.54 (m respectively, 2H respectively, $C_6H_4$). $^{13}$C-NMR ($C_6D_6$, TMS): δ −1.1 (Si$CH_3$), 9.3 (Si$CH_2$), 19.6 (SiC$\underline{C}$), 101.3 (d, J$_{FC}$=1.7 Hz, CH=), 115.0 (d, J$_{FC}$=21.4 Hz, F$\underline{CC}$), 126.5 (d, J$_{FC}$=7.9 Hz), F$\underline{CCC}$), 134.6 (d, J$_{FC}$=3.2 Hz, F$\underline{CCCC}$), 150.0 (O—C=), 162.8 (d, J$_{FC}$=245.8 Hz, FC). $^{29}$Si-NMR ($C_6D_6$, TMS): δ 18.4 IR (liquid film): 1638 (C=C), 1255 (SiMe), 1089 (SiO) cm$^{-1}$. MS (EI, 70 eV): m/z 222 (100, M$^+$), 221 (69), 207 (84), 148 (75), 147 (45), 96 (29), 75 (36), 59 (22). Elementary analysis for $C_{12}H_{16}OSi$ Found: C, 64.55%; H, 6.85% Calculated: C, 64.83%; H, 6.80%

2,2-dimethyl-6-(2-furyl)-1-oxa-2-sila-5-cyclohexene (product of Example 6)

Boiling point: 107°–114° C./7 mmHg (Kügelrohr). $^1$H-NMR (C$_6$D$_6$, TMS): δ 0.11 (s, 6H, Si(CH$_3$)$_2$), 0.58 (t, J=7.1 Hz, 2H, SiCH$_2$), 2.23 (td, J=7.1, 4.9 Hz, 2H, SiCCH$_2$), 5.61 (t, J=4.9 Hz, 1H, CH=), 6.10–6.14, 6.53–6.56 and 7.01–7.07 (m respectively, 1H respectively, H of furyl group). $^{13}$C-NMR (C$_6$D$_6$, TMS): δ −1.2 (SiCH$_3$), 9.4 (SiCH$_2$), 19.2 (SiC$\underline{C}$), 100.8 (CH=), 105.5, 111.3 and 141.7 (tertiary C of furyl group), 144.0 (quaternary C of furyl group), 153.0 (O—C=). $^{29}$Si-NMR (C$_6$D$_6$, TMS): δ 18.6 IR (liquid film): 1680 (C=C), 1255 (SiMe), 1056 (SiO) cm$^{-1}$. MS (EI, 70 eV): m/z 194 (100, M$^+$), 193 (42), 179 (34), 153 (27), 151 (20), 120 (22), 119 (22), 91 (40), 82 (26), 75 (65), 45 (25), 43 (24). HR-MS (EI, 70 eV): Found: 194.0771; Calculated: 194.0762 ($C_{10}H_{14}O_2Si$).

2,2-dimethyl-6-styryl-1-oxa-2-sila-5-cyclohexene (product of Example 7)

Boiling point: 170°–177° C./7 mmHg (Kügelrohr). $^1$H-NMR (C$_6$D$_6$, TMS): δ 0.16 (s, 6H, Si(CH$_3$)$_2$), 0.62 (t, J=7.1 Hz, 2H, SiCH$_2$), 2.26 (td, J=7.1, 4.9 Hz, 2H, SiCCH$_2$), 4.87 (t, J=4.9 Hz, 1H, CH=C—O), 6.58 and 7.25 (d respectively, J=15.6 Hz, 1H respectively, CH=CH), 6.98–7.14 (m, 3H, H of benzene ring), 7.29–7.35 (m, 2H, H of benzene ring). $^{13}$C-NMR (C$_6$D$_6$, TMS): δ −1.1 (SiCH$_3$), 9.4 (SiCH$_2$), 20.1 (SiC$\underline{C}$), 108.2 (O—C=$\underline{C}$H), 126.9 (tertiary C, 3C), 127.0 (tertiary C, 1C), 127.4 (tertiary C, 1C), 128.8 (tertiary C of benzene ring, 2C), 137.9 (quaternary C of benzene ring), 151.1 (O—C=). $^{29}$Si-NMR (C$_6$D$_6$, TMS): δ 18.0 IR (liquid film): 1663 (C=C), 1255 (SiMe), 1062 (SiO) cm$^{-1}$. MS (EI, 70 eV): m/z 230 (100, M$^+$), 229 (29), 215 (25), 202 (81), 201 (50), 189 (26), 155 (22), 153 (20), 141 (35), 128 (56), 115 (28), 77 (25), 75 (72), 59 (37), 45 (25), 43 (21). HR-MS (EI, 70 eV): Found: 230.1107; Calculated: 230.1125 ($C_{14}H_{18}OSi$).

2,2-dimethyl-6-cyclohexyl-1-oxa-2-sila-5-cyclohexene (product of Example 8)

Boiling point: 99°–106° C./7 mmHg (Kügelrohr). $^1$H-NMR (C$_6$D$_6$, TMS): δ 0.15 (s, 6H, Si(CH$_3$)$_2$), 0.64 (t, J=7.2 Hz, 2H, SiCH$_2$), 1.05–2.13 (m, 11H, C$_6$H$_{11}$), 2.20 (td, J=7.1, 4.6 Hz, 2H, SiCCH$_2$), 4.58 (t, J=4.6 Hz, 1H, CH=). $^{13}$C-NMR (C$_6$D$_6$, TMS): δ −1.1 (SiCH$_3$), 10.1 (SiCH$_2$), 19.2 (SiC$\underline{C}$), 26.7 (CH$_2$, 2C), 31.2 (CH$_2$), 44.8 (CH), 97.9 (CH=), 158.2 (O—C=). $^{29}$Si-NMR (C$_6$D$_6$, TMS): δ 16.5. IR (liquid film): 1659 (C=C), 1253 (SiMe), 1069 (SiO) cm$^{-1}$. MS (EI, 70 eV): m/z 210 (22, M$^+$), 169 (17), 155 (100), 142 (35), 127 (66), 75 (66), 59 (20). Elementary analysis for $C_{12}H_{22}OSi$ Found: C, 68.54%; H, 10.58% Calculated: C, 68.51%; H, 10.54%

Example 9

The reaction and analysis of Example 1 were repeated, except that, instead of 1,1-dimethyl-1-silacyclobutane, 1,1-diphenyl-1-silacyclobutane was used, and it was estimated that 2,2-diphenyl-6-phenyl-1-oxa-2-sila-5-cyclohexene was produced in a yield of 98%. Similarly to Example 1, the post-treatment was carried out, thereby obtaining the intended product in an amount of ~1.4 mmol (an isolated yield of ~70%).

This compound is a novel compound that has not yet appeared in the literature, and the values of the physical properties and the spectral data thereof are as follows:

Boiling point: 210°–226° C./0.1 mmHg (Kügelrohr).

$^1$H-NMR (C$_6$D$_6$, TMS): δ 1.17 (t, J=7.1 Hz, 2H, SiCH$_2$), 2.32 (td, J=7.1, 4.9 Hz, 2H, SiCCH$_2$), 5.43 (t, J=4.9 Hz, 1H, CH=), 7.05–7.84 (m, 15H, C$_6$H$_5$). $^{13}$C-NMR (C$_6$D$_6$, TMS): δ 7.7 (SiCH$_2$), 19.8 (SiC$\underline{C}$), 102.2 (CH=), 124.9, 127.9, 128.36, 128.42, 130.53, 134.7, 134.9, 138.1, 151.2 (O—C=). $^{29}$Si-NMR (C$_6$D$_6$, TMS): δ −4.4. IR (liquid film): 1678 (C=C), 1222 (SiMe), 1118 (SiO) cm$^{-1}$. MS (EI, 70 eV): m/z 328 (62, M$^+$), 313 (17), 250 (100), 224 (16), 223 (15), 199 (14), 181 (19), 130 (41), 129 (22), 128 (15), 125 (18), 115 (14), 105 (50), 77 (28), 53 (15), 51 (13), 45 (19). HR-MS (EI, 70 eV): Found: 328.1285; Calculated: 328.1282 ($C_{22}H_{20}OSi$).

Example 10

The reaction and analysis of Example 1 were repeated, except that, instead of 1,1-dimethyl-1-silacyclobutane and benzoyl chloride, 1,1-diphenyl-1-silacyclobutane and p-toluoyl chloride were respectively used, and it was estimated that 2,2-diphenyl-6-(p-tolyl)-1-oxa-2-sila-5-cyclohexene was produced in a yield of ~95%. Similarly to Example 1, the post-treatment was carried out, thereby obtaining the intended product in an amount of ~1.5 mmol (an isolated yield of ~75%).

This compound is a novel compound that has not yet appeared in the literature, and the values of the physical properties and the spectral data thereof are as follows:

Boiling point: ~220° C./0.1 mmHg (Kügelrohr).

$^1$H-NMR (C$_6$D$_6$, TMS): δ 1.18 (t, J=7.1 Hz, 2H, SiCH$_2$), 2.11 (s, 3H, CH$_3$), 2.34 (td, J=7.1, 4.9 Hz, 2H, SiCCH$_2$), 5.44 (t, J=4.9. Hz, 1H, CH=), 7.07–7.25 and 7.60–7.83 (m respectively, 2H respectively, C$_6$H$_4$). $^{13}$C-NMR (C$_6$D$_6$, TMS): δ 7.8 (SiCH$_2$), 19.8 (SiC$\underline{C}$), 21.1 (CH$_3$), 101.4 (CH=), 124.9, 128.3, 129.2, 130.5, 134.7, 135.0, 135.4, 137.4, 151.4 (O—C=). $^{29}$Si-NMR (C$_6$D$_6$, TMS): δ −4.1. MS (EI, 70 eV): m/z 342 (100, M$^+$), 327 (56), 264 (91), 249 (24), 238 (21), 199 (37), 181 (24), 144 (25), 132 (31), 129 (43), 105 (44), 77 (22), 45 (22).

Example 11

A mixture of 0.15 mmol of 1,1-diphenyl-1-silacyclobutane, 0.15 mmol of p-toluoyl chloride, 0.003 mmol of dichlorobis(benzonitrile)palladium, 0.30 mmol of triethylamine, and 0.5 ml of toluene was heated under nitrogen in a sealed tube at 80° C. for about 10 min. By analyzing the reaction solution by gas chromatography, it was estimated that 2,2-diphenyl-6-(p-tolyl)-1-oxa-2-sila-5-cyclohexene was produced in a yield of ~90%.

Example 12

A mixture of 0.15 mmol of 1,1-diphenyl-1-silacyclobutane, 0.15 mmol of p-toluoyl chloride, 0.003 mmol of dichlorobis(trimethylphosphine)palladium, and 0.30 ml of triethylamine was heated under nitrogen in a sealed tube at 120° C. for about 5 hours. By analyzing the reaction solution by gas chromatography, it was estimated that 2,2-diphenyl-6-(p-tolyl)-1-oxa-2-sila-5-cyclohexene was produced in a yield of ~80%.

Example 13

A mixture of 2.0 mmol of 1,1-dimethyl-1-silacyclobutane, 1.0 mmol of terephthaloyl dichloride, 0.08 mmol of dichlorobis(benzonitrile)palladium, 4.0 mmol of triethylamine, and 2 ml of toluene was stirred under nitrogen in a Schlenk tube at 80° C. for 1 hour. By measuring the reaction solution by NMR, it was estimated that bis(2,2-dimethyl-1-oxa-2-sila-5-cyclohexen-6-yl)-p-phenylene was produced in a yield of 96%. The reaction mixture was concentrated under reduced pressure, and the product was extracted with ~10 ml of hexane. The hexane extract was concentrated under reduced pressure, followed by recrystallization from hexane, thereby obtaining the intended product in an amount of 0.71 mmol (an isolated yield of 71%).

This compound is a novel compound that has not yet appeared in the literature, and the values of the physical properties and the spectral data thereof are as follows:

Melting point: 74°–75° C. (under nitrogen). $^1$H-NMR ($C_6D_6$, TMS): δ 0.15 (s, 12H, Si($CH_3$)$_2$), 0.63 (t, J=7.1 Hz, 4H, Si$CH_2$), 2.27 (td, J=7.1, 4.9 Hz, 4H, SiC$CH_2$), 5.41 (t, J=4.9 Hz, 2H, CH=), 7.78 (s, 4H, $C_6H_4$). $^{13}$C-NMR ($C_6D_6$, TMS): δ −1.0 (Si$CH_3$), 9.5 (Si$CH_2$), 19.8 (Si$C\underline{C}$), 101.7 (CH=), 124.6 (tertiary C of benzene ring), 137.5 (quaternary C of benzene ring), 150.8 (O—C=). $^{29}$Si-NMR ($C_6D_6$, TMS): δ 18.1. MS (EI, 70 eV): m/z 330 (100, M$^+$), 329 (39), 315 (21), 255 (21), 203 (88), 75 (54), 59 (32). Elementary analysis for $C_{18}H_{26}O_2Si_2$ Found: C, 65.41%; H, 7.96% Calculated: C, 65.40%; H, 7.93%

Example 14

The reaction and analysis of Example 1 were repeated, except that, instead of benzoyl chloride and triethylamine, heptanoyl chloride and diisopropylethylamine were respectively used, and it was estimated that 2,2-dimethyl-6-hexyl-1-oxa-2-sila-5-cyclohexene was produced, in a yield of ~82%. Similarly to Example 1, the post-treatment was carried out, thereby obtaining the intended product in an isolated yield of 77%.

This compound is a novel compound that has not yet appeared in the literature, and the values of the physical properties and the spectral data thereof are as follows:

Boiling point: ~124° C./8 mmHg (Kügelrohr). $^1$H-NMR ($C_6D_6$, TMS): δ 0.13 (s, 6H, Si$CH_3$), 0.63 (t, J=7.1 Hz, 2H, $CH_2$Si), 0.82–0.93 (m, 3H, $CH_2C\underline{H_3}$), 1.23–1.35 (m, 8H, $CH_2$), 1.54–1.62 (m, 2H, O—C$CH_2$), 2.13–2.36 (m, 2H, $CH_2$CSi), 4.54 (t, J=4.4 Hz, 1H, =CH). $^{13}$C-NMR ($C_6D_6$, TMS): δ −1.1 (Si$CH_3$), 9.7 ($CH_2$Si), 14.30, 19.3, 23.0, 27.4, 29.2, 32.2, 36.9, 99.7 (=CH), 153.9 (=CO). $^{29}$Si-NMR ($C_6D_6$, TMS): δ 16.4. MS (EI, 70 eV): m/z 212 (11, M$^+$), 155 (44), 142 (100), 127 (60), 114 (48), 99 (15), 75 (54), 73 (10), 61 (10), 59 (18), 47 (11), 45 (17), 43 (19), 41 (20). IR (liquid film): 1717 (s), 1661 (m), 1462 (m), 1410 (m), 1371 (m), 1344 (m), 1255 (s, SiMe), 1195 (m), 1131 (s), 1062 (s), 975 (m), 924 (s), 841 (s) cm$^{-1}$. HR-MS (EI, 70 eV): Found:212.1612; Calculated: 212.1595 ($C_{12}H_{24}$OSi).

Example 15

The reaction and analysis of Example 14 were repeated, except that, instead of diisopropylethylamine, dicyclohexylethylamine was used, and it was estimated that 2,2-dimethyl-6-hexyl-1-oxa-2-sila-5-cyclohexene was produced in a yield of ~65%.

Example 16

Example 1 was repeated, except that, instead of benzoyl chloride and triethylamine, hydrocinnamoyl chloride and diisopropylethylamine were respectively used, and that the reaction was carried out for 30 min. From the results of the NMR analysis, it was estimated that 2,2-dimethyl-6-(2-phenylethyl)-1-oxa-2-sila-5-cyclohexene was produced in a yield of ~55%.

Example 17

The reaction and analysis of example 16 were repeated, except that the reaction time was 8 hours. It was estimated that 2,2-dimethyl-6-(2-phenylethyl)-1-oxa-2-sila-5-cyclohexene was produced in a yield of ~66%. Similarly to Example 1, the post-treatment was carried out, and the intended product was isolated in a yield of 61%.

This compound is a novel compound that has not yet appeared in the literature, and the values of the physical properties and the spectral data thereof are as follows:

Boiling point: ~154° C./6 mmHg (Kügelrohr). $^1$H-NMR ($C_6D_6$, TMS): δ 0.14 (s, 6H, Si$CH_3$), 0.59 (t, J=7.1 Hz, 2H, $CH_2$Si), 2.11 (dt, J=4.4, and 7.1 Hz, 2H, SiC$CH_2$), 2.39 and 2.87 (t respectively, J=7.8 Hz, 2H respectively, $CH_2CH_2$C—O) 4.46 (t, J=4.4 Hz, 1H, =CH), 7.02–7.24 (m, 5H, $C_6H_5$). $^{13}$C-NMR ($C_6D_6$, TMS): δ −1.1 (Si$CH_3$), 9.4 ($CH_2$Si), 19.2 ($\underline{C}H_2$CSi), 34.0 and 39.0 ($\underline{C}H_2\underline{C}H_2$C=), 100.3 (=CH), 126.0 (o-C), 128.5 (p-C), 128.8 (m-C), 142.3 (ipso-C), 152.8 (=CO). $^{29}$Si-NMR ($C_6D_6$, TMS): δ 16.9. IR (liquid film): 1661 (s), 1456 (m), 1344 (m), 1255 (s, SiMe), 1193 (s), 1064 (s), 998 (m), 967 (s), 872 (s), 845 (s), 799 (s), 772 (m), 750 (m), 698 (s) cm$^{-1}$. MS (EI, 70 eV): m/z 232 (67, M$^+$), 141 (48), 127 (59), 99 (39), 91 (77), 75 (100), 65 (18), 59 (24), 45 (21). HR-MS (EI, 70 eV): Found: 232.1291; Calculated: 232.1282 ($C_{14}H_{20}$OSi).

Example 18

The reaction of Example 16 was repeated, except that, instead of diisopropylethylamine, isopropyldiethylamine was used, and it was estimated that 2,2-dimethyl-6-(2-phenylethyl)-1-oxa-2-sila-5-cyclohexene was produced in a yield of ~28%.

Example 19

The reaction and analysis of Example 1 were repeated, except that, instead of benzoyl chloride and triethylamine, 10-undecenoyl chloride and diisopropylethylamine were used respectively, and it was estimated that 2,2-dimethyl-6-(9-decenyl)-1-oxa-2-sila-5-cyclohexene was produced in a yield of ~79%. Similarly to Example 1, the post-treatment was carried out, thereby obtaining the intended product in an isolated yield of 75%.

This compound is a novel compound that has not yet appeared in the literature, and the values of the physical properties and the spectral data thereof are as follows:

Boiling point: ~168° C./6 mmHg (Kügelrohr). $^1$H-NMR ($C_6D_6$, TMS): δ 0.14 (s, 6H, Si$CH_3$), 0.63 (t, J=7.1 Hz, 2H, $CH_2$Si), 1.16–1.38 (m, 12H, $CH_2$), 1.97 (dt, J=4.4 and 7.1 Hz, 2H, $CH_2$CSi), 2.07–2.22 (m, 4H, O—C$CH_2$ and $CH_2$=CH—$C\underline{H_2}$), 4.56 (t, J=4.4 Hz, 1H, O—C=CH), 4.92–5.03 (m, 2H, $C\underline{H_2}$=CH), 5.69–5.86 (m, 1H, $CH_2$=C$\underline{H}$). $^{13}$C-NMR ($C_6D_6$, TMS): δ −1.1 (Si$CH_3$), 9.7 ($CH_2$Si), 19.4, 27.5, 29.3, 29.5, 29.87, 29.90, 34.2, 99.7 (=CH), 114.4 ($\underline{C}H_2$=CH—), 139.2 ($CH_2$=$\underline{C}H$—), 153.9 (=CO). $^{29}$Si-NMR ($C_6D_6$, TMS): δ 16.5. IR (liquid film): 1661 (s), 1340 (m), 1253 (s, SiMe), 1195 (s), 1056 (m), 967 (s), 924 (m), 911 (m), 874 (m), 843 (s), 797 (s), 762 (m) cm$^{-1}$. MS (EI, 70 eV): m/z 266 (5, M$^+$), 155 (48), 142 (100), 129 (69), 127 (40), 114 (31), 101 (25), 99 (13), 75 (66), 61 (12), 59 (19), 55 (16), 45 (12), 43 (11), 41 (34). HR-MS (EI, 70 eV): Found: 266.2034; Calculated: 266.2064 ($C_{16}H_{30}$OSi).

Having described our invention as related to the present embodiments, it is our intention that the invention not be limited by any of the details of the description, unless otherwise specified, but rather be construed broadly within its spirit and scope as set out in the accompanying claims.

What we claim is:

1. A method of preparing cyclic silyl enol ethers represented by formula (IV):

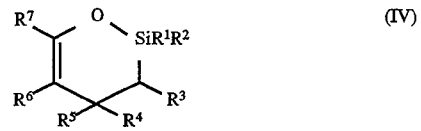

wherein $R^1$ and $R^2$ which are the same or different, each represent a monovalent group selected from an alkyl group, an aryl group, and an aralkyl group; $R^3$, $R^4$, $R^5$, and $R^6$, which are the same or different, each represent a monovalent group selected from a hydrogen atom, an alkyl group, and an aryl group; and $R^7$ represents an aryl group, an alkenyl group, an alkyl group, or a monovalent heterocyclic group, or by formula (V-a) or (V-b):

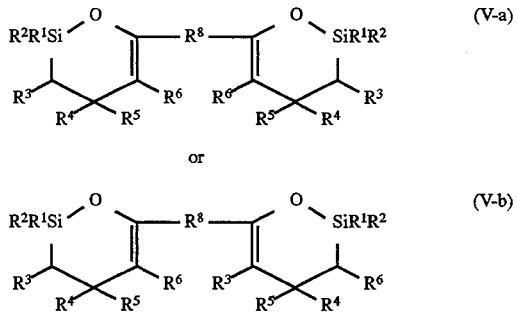

wherein $R^1$, $R^2$, $R^3$, $R^4$, $R^5$, and $R^6$ are as defined above, and $R^8$ represents an arylene group, an alkenylene group, an alkylene group, or a divalent heterocyclic group, comprising reacting a silacyclobutane represented by formula (I):

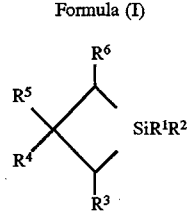

wherein $R^1$, $R^2$, $R^3$, $R^4$, $R^5$, and $R^6$ have the same meanings as defined above in formula (IV), (V-a), or (V-b), with an acid halide represented by formula (II):

wherein $R^7$ has the same meaning as defined above in formula (IV), and X represents a halogen atom, or by formula (III):

wherein $R^8$ has the same meaning as defined above in formula (V-a) or (V-b), and X' represents a halogen atom, in the presence of a palladium catalyst and an organic base.

2. The method of preparing cyclic silyl enol ethers as claimed in claim 1, wherein, in formula (I), $R^1$ and $R^2$ each represent an alkyl group having 1 to 20 carbon atoms, an aryl group having 6 to 20 carbon atoms, or an aralkyl group having 7 to 20 carbon atoms; and $R^3$, $R^4$, $R^5$, and $R^6$ each represent a hydrogen atom, an alkyl group having 1 to 10 carbon atoms, or an aryl group having 6 to 20 carbon atoms.

3. The method of preparing cyclic silyl enol ethers as claimed in claim 1, wherein, in formula (I), $R^1$ and $R^2$ each are a methyl group, an ethyl group, an isopropyl group, a pentyl group, an octyl group, a phenyl group, a naphthyl group, a benzyl group, or a phenethyl group; and $R^3$, $R^4$, $R^5$, and $R^6$ each are a hydrogen atom, a methyl group, a butyl group, a phenyl group, or a naphthyl group.

4. The method of preparing cyclic silyl enol ethers as claimed in claim 1, wherein, in formula (II), $R^7$ represents an aryl group having 6 to 20 carbon atoms, an alkenyl group having 2 to 20 carbon atoms, an alkyl group having 1 to 20 carbon atoms, or a 3- to 10-membered monovalent heterocyclic group having at least one heteroatom selected from oxygen atom, nitrogen atom, sulfur atom, selenium atom, silicon atom, and boron atom; and X is a chlorine atom, a bromine atom, or an iodine atom.

5. The method of preparing cyclic silyl enol ethers as claimed in claim 1, wherein, in formula (II), $R^7$ is a phenyl group, a naphthyl group, a vinyl group, a styryl group, a decenyl group, a 2-phenylethyl group, an isopropyl group, a hexyl group, a cyclohexyl group, a tert-butyl group, a furyl group, or a thienyl group; and X is a chlorine atom, a bromine atom, or an iodine atom.

6. The method of preparing cyclic silyl enol ethers as claimed in claim 1, wherein, in formula (III), $R^8$ represents an arylene group having 6 to 20 carbon atoms, an alkenylene group having 2 to 20 carbon atoms, an alkylene group having 1 to 20 carbon atoms, or a 3- to 10-membered divalent heterocyclic group having at least one heteroatom selected from oxygen atom, nitrogen atom, sulfur atom, selenium atom, silicon atom, and boron atom; and X' is a chlorine atom, a bromine atom, or an iodine atom.

7. The method of preparing cyclic silyl enol ethers as claimed in claim 1, wherein, in formula (III), $R^8$ is a phenylene group, a naphthylene group, a vinylene group, a propenylene group, a methylmethylene group, a 1,2-dimethylethylene group, a 1,3-diethyltrimethylene group, a furylene group, or a thienylene group; and X' is a chlorine atom, a bromine atom, or an iodine atom.

8. The method of preparing cyclic silyl enol ethers as claimed in claim 1, wherein the molar ratio of the silacyclobutane to the haloformyl group of the acid halide is 1 or more.

9. The method of preparing cyclic silyl enol ethers as claimed in claim 1, wherein the palladium catalyst is selected from palladium complexes, palladium metal salts, palladium metal, and supported palladium metal.

10. The method of preparing cyclic silyl enol ethers as claimed in claim 1, wherein the molar ratio of the palladium catalyst to the silacyclobutane or the acid halide is in the range from 0.0001 to 0.5.

11. The method of preparing cyclic silyl enol ethers as claimed in claim 1, wherein the organic base is selected from amines.

12. The method of preparing cyclic silyl enol ethers as claimed in claim 1, wherein the molar ratio of the organic base to the haloformyl group in the acid halide is 1 or more.

13. A cyclic silyl enol ether represented by formula (VI):

Formula (VI)

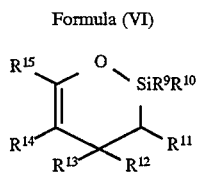

(VI)

wherein $R^9$ and $R^{10}$, which are the same or different, each represent a monovalent group selected from an alkyl group, an aryl group, and an aralkyl group; $R^{11}$, $R^{12}$, $R^{13}$, and $R^{14}$, which are the same or different, each represent a monovalent group selected from a hydrogen atom, an alkyl group, and an aryl group; and $R^{15}$ represents an aryl group, an alkenyl group, an alkyl group, or a monovalent heterocyclic group, or by formula (VII-a) or (VII-b):

Formula (VII-a), (VII-b)

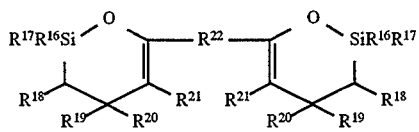

(VII-a)

or

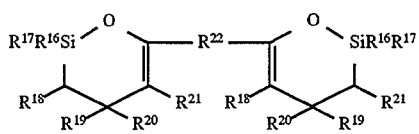

(VII-b)

wherein $R^{16}$ and $R^{17}$, which are the same or different, each represent a monovalent group selected from an alkyl group, an aryl group, and an aralkyl group; $R^{18}$, $R^{19}$, $R^{20}$, and $R^{21}$, which are the same or different, each represent a monovalent group selected from a hydrogen atom, an alkyl group, and an aryl group; and $R^{22}$ represents an arylene group.

14. The cyclic silyl enol ether as claimed in claim 13, wherein in formula (VI), $R^9$ and $R^{10}$ each are a methyl group, an ethyl group, an isopropyl group, a pentyl group, an octyl group, a phenyl group, a naphthyl group, a benzyl group, or a phenethyl group; $R^{11}$, $R^{12}$, $R^{13}$, and $R^{14}$ each are a hydrogen atom, a methyl group, or a phenyl group; and $R^{15}$ is a phenyl group, a tolyl group, an anisyl group, a fluorophenyl group, a naphthyl group, a vinyl group, a styryl group, a decenyl group, a 2-phenylethyl group, an isopropyl group, a hexyl group, a cyclohexyl group, a tert-butyl group, a furyl group, or a thienyl group.

15. The cyclic silyl enol ether as claimed in claim 13, wherein the cyclic silyl enol ether represented by formula (VI) is 2,2-dimethyl-6-phenyl-1-oxa-2-sila-5-cyclohexene, 2,2-dimethyl-6-tolyl-1-oxa-2-sila-5-cyclohexene, 2,2-dimethyl-6-anisyl-1-oxa-2-sila-5-cyclohexene, 2,2-dimethyl-6-fluorophenyl-1-oxa-2-sila-5-cyclohexene, 2,2-dimethyl-6-naphthyl-1-oxa-2-sila-5-cyclohexene, 2,2-dimethyl-6-cyclohexyl-1-oxa-2-sila-5-cyclohexene, 2,2-dimethyl-6-furyl-1-oxa-2-sila-5-cyclohexene, 2,2-dimethyl-6-thienyl-1-oxa-2-sila-5-cyclohexene, 2-methyl-2,6-diphenyl-1-oxa-2-sila-5-cyclohexene, 2,2-diphenyl-6-tolyl-1-oxa-2-sila-5-cyclohexene, 2,2-dimethyl-6-styryl-1-oxa-2-sila-5-cyclohexene, 2,2,6-triphenyl-1-oxa-2-sila-5-cyclohexene, 2,2-dimethyl-6-hexyl-1-oxa-2-sila-5-cyclohexene, 2,2-dimethyl-6-(2-phenylethyl)-1-oxa-2-sila-5-cyclohexene, or 2,2-dimethyl-6-(9-decenyl)-1-oxa-2-sila-5-cyclohexene.

16. The cyclic silyl enol ether as claimed in claim 13, wherein in formulae (VII-a) and (VII-b), $R^{16}$ and $R^{17}$ each are a methyl group, an ethyl group, an isopropyl group, a pentyl group, an octyl group, a phenyl group, a naphthyl group, a benzyl group, or a phenethyl group; $R^{18}$, $R^{19}$, $R^{20}$, and $R^{21}$ each are a hydrogen atom, a methyl group, or a phenyl group; and $R^{22}$ represents a phenylene group or a naphthylene group.

17. The cyclic silyl enol ether as claimed in claim 13, wherein the cyclic silyl enol ether represented by formula (VII-a) or (VII-b) is bis(2,2-dimethyl-1-oxa-2-sila-5-cyclohexen-6-yl)-p- or -m-phenylene, or bis(2,2-dimethyl-1-oxa-2-sila-5-cyclohexen-6-yl)-1,4- or -1,5-naphthylene.

* * * * *